United States Patent
Kusanagi et al.

(10) Patent No.: US 7,157,428 B2
(45) Date of Patent: *Jan. 2, 2007

(54) METHOD FOR TREATMENT AND REPAIR OF MENISCAL INJURIES

(75) Inventors: Akihiko Kusanagi, Brookline, MA (US); Mary Beth Schmidt, Pomfret Center, CT (US); Laurence J. B. Tarrant, Northampton, MA (US)

(73) Assignee: Histogenics, Corp., Northampton, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 10/998,230

(22) Filed: Nov. 26, 2004

(65) Prior Publication Data

US 2006/0069011 A1 Mar. 30, 2006

Related U.S. Application Data

(60) Provisional application No. 60/525,247, filed on Nov. 26, 2003.

(51) Int. Cl.
*A61K 38/39* (2006.01)
*C07K 14/78* (2006.01)

(52) U.S. Cl. .............................. 514/12; 530/356

(58) Field of Classification Search ................ None
See application file for complete search history.

(56) References Cited

U.S. PATENT DOCUMENTS 5,306,500 A * 4/1994 Rhee et al. ................ 424/422
2005/0043814 A1 * 2/2005 Kusanagi et al. ........ 623/23.58

FOREIGN PATENT DOCUMENTS

EP 1264607 A1 11/2002
EP 1264607 A1 * 12/2002

* cited by examiner

*Primary Examiner*—Robert A. Wax
(74) *Attorney, Agent, or Firm*—Hana Verny; Verny, Jones, Schmitt & Aston, LLP

(57) ABSTRACT

A method for repair of meniscal injuries comprising induction of meniscal regeneration by introducing a strongly adhesive collagen-polyethylene glycol (PEG) hydrogel to a site of injury.

17 Claims, 5 Drawing Sheets

Figure 1: Porcine meniscus in culture
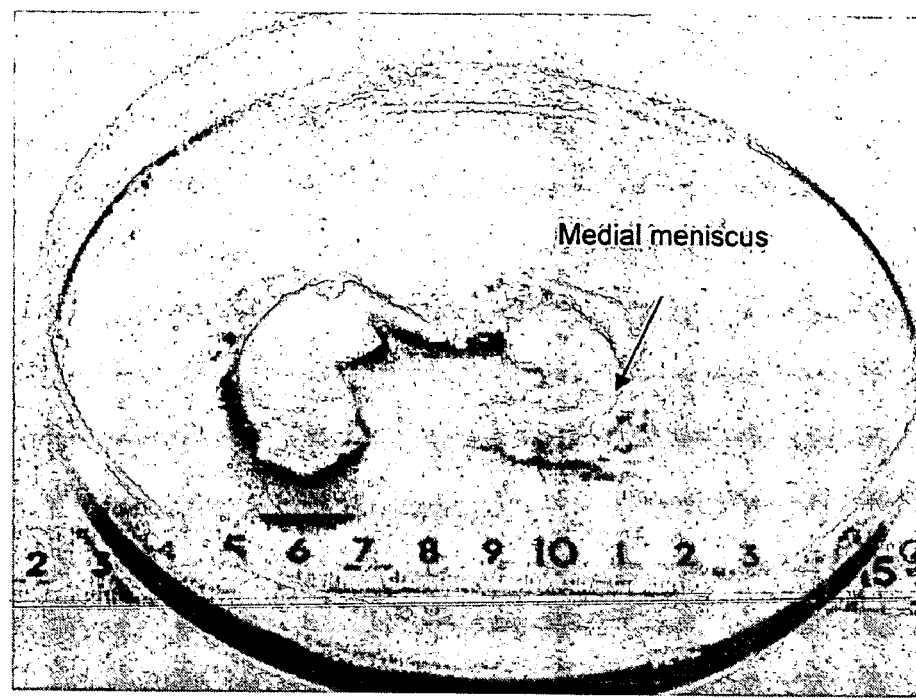
Figure 2: Tear sites with treatment group assignments indicated
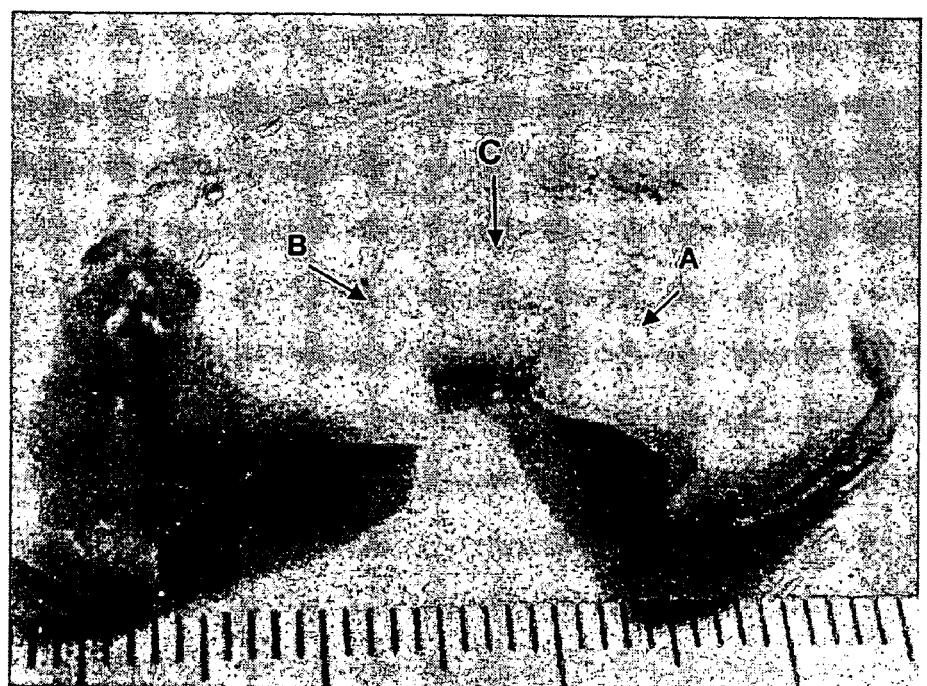

Figure 3a: No treatment (4x)*
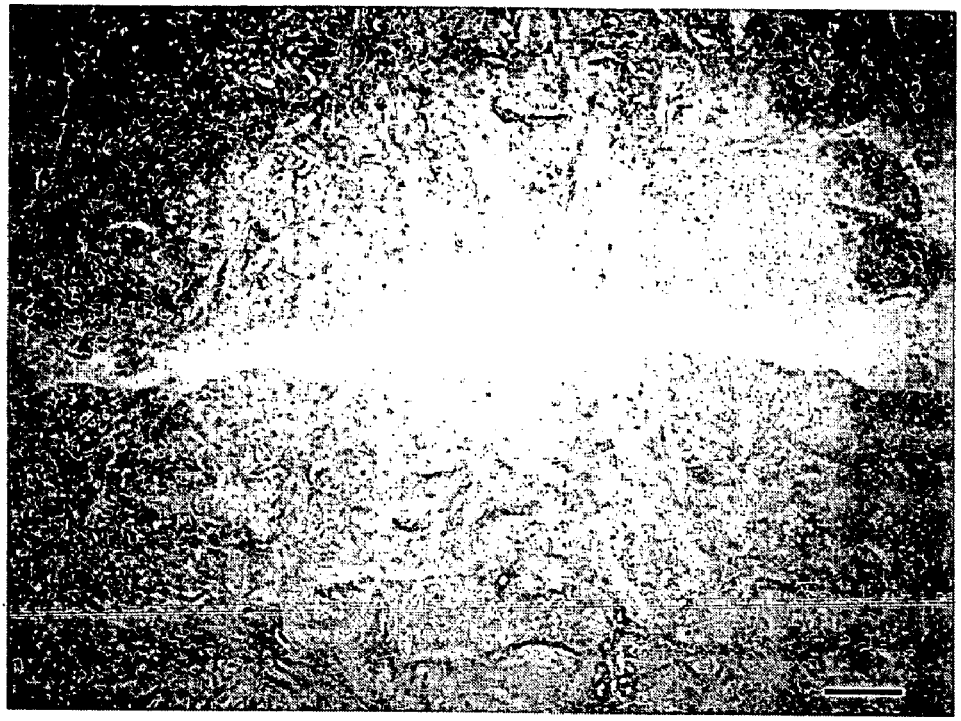
Figure 3b: No treatment (10x)*
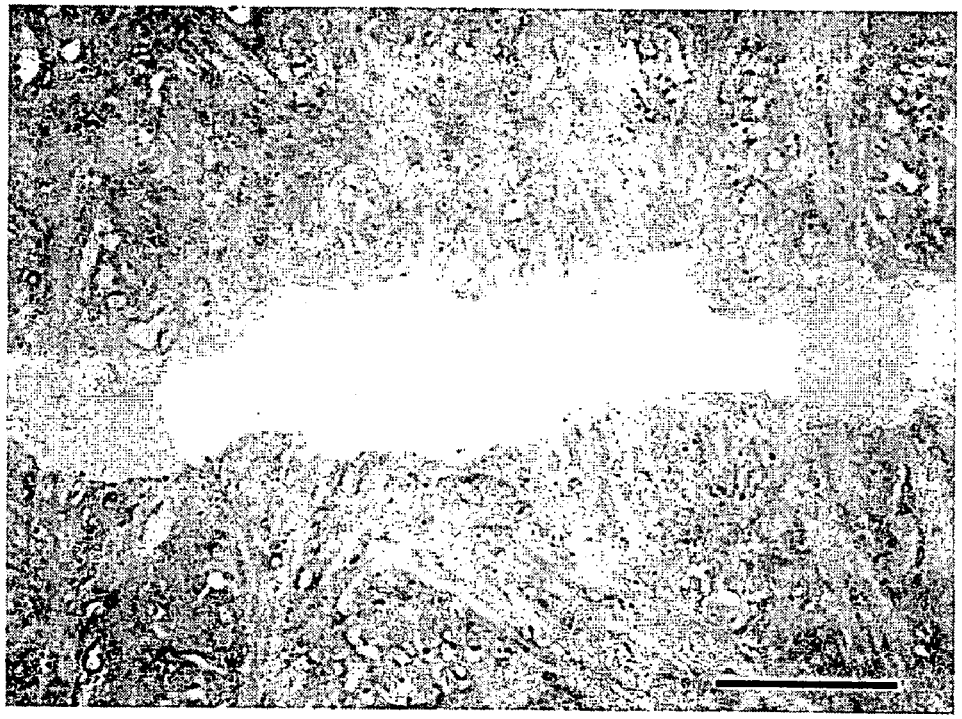
*Scale: 250 micro meter

Figure 4a: Suture (4x)*
Figure 4b: Suture (10x)*
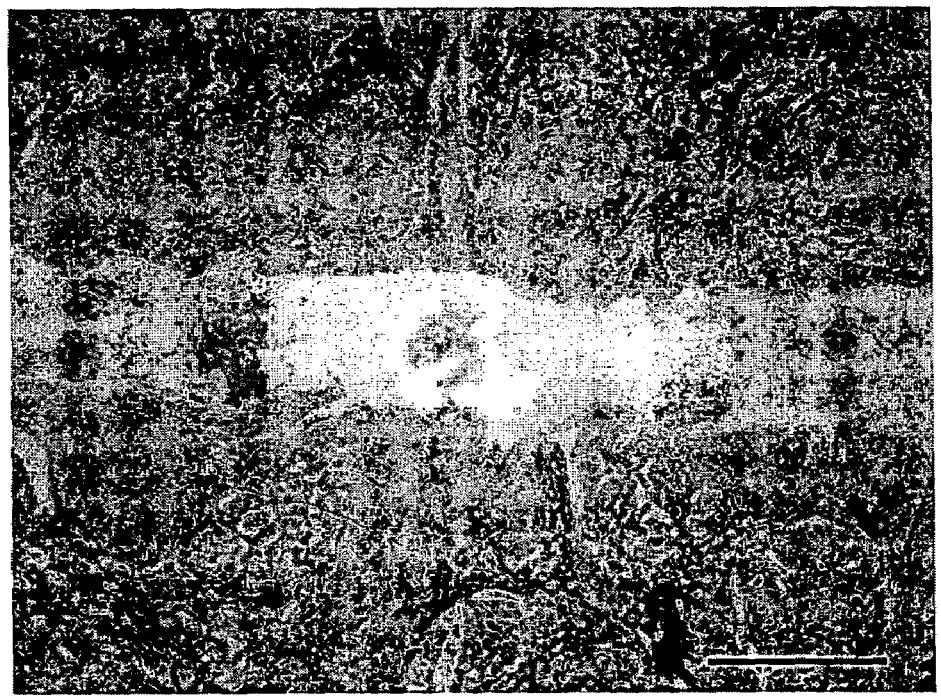
*Scale: 250 micro meter

Figure 5 Collagen-PEG hydrogel (4x)*
Figure 5b: Collagen-PEG hydrogel (10x)*
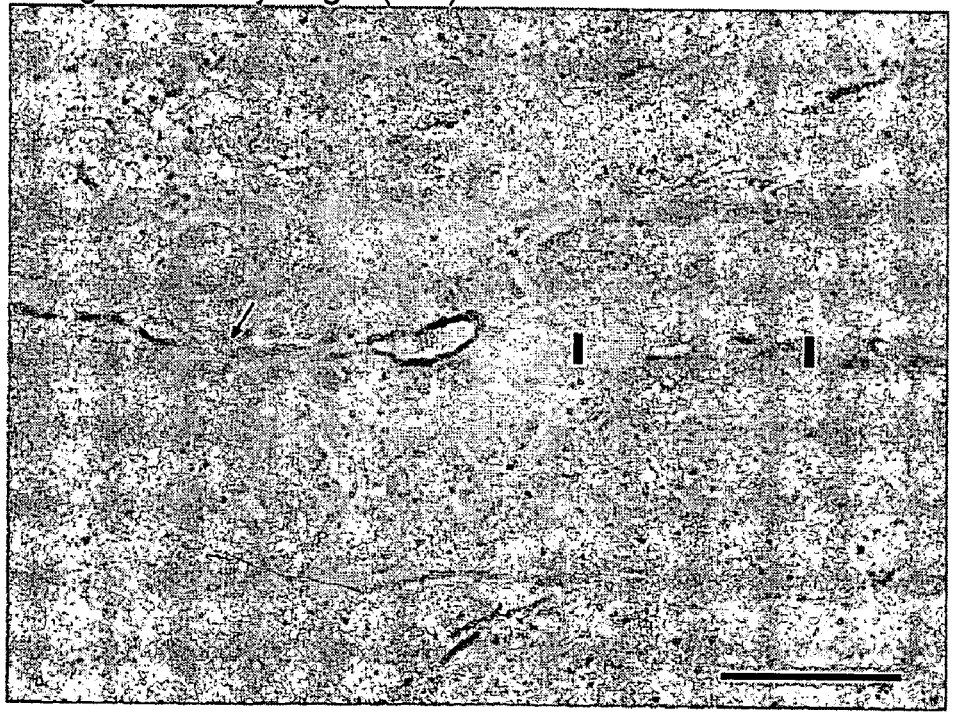
*Scale: 250 micro meter, arrow: Collagen-PEG hydrogel
I: cell integration Figure 6: Sinclair swine medial meniscus

METHOD FOR TREATMENT AND REPAIR OF MENISCAL INJURIES

This application is based on and claims priority of the Provisional Application Ser. No. 60/525,247, filed on Nov. 26, 2003.

BACKGROUND OF THE INVENTION

Field of the Invention

This invention concerns a method for repair of meniscal injuries. In particular, the invention concerns a minimally invasive method for repair of meniscal injuries comprising induction of meniscal regeneration by introducing an adhesive collagen-polyethylene glycol (PEG) hydrogel to a site of injury. The collagen-PEG hydrogels strongly bind the torn region of the meniscus for a period of time needed for healing and promote cell migration and extracellular matrix formation in the torn zone.

BACKGROUND AND RELATED DISCLOSURES

Repair of meniscal injuries is one of the most common operative procedures utilized in orthopedics surgery today (Koski J A, Ibarra C, Rodeo S A, Warren R F: Meniscal Injury and Repair—Clinical Status. *Tissue Engr. Orthop. Surg.*, 31(3):419–435 (2000)).

Meniscal tears are common in young individuals, usually as a result of sports-related activities, as well as in older population suffering from degenerative joint diseases. The meniscus plays an important role in load transmission, shock absorption and knee joint stability. Injuries to the meniscus cause pain, disability and damage to the articular cartilage on the femoral and tibial surfaces, leading to development of degenerative changes and osteoarthritis.

Early treatments for meniscal injuries typically consists of partial or total meniscectomy. This approach frequently results in accelerated cartilage degeneration due to decreased joint contact area and the resultant rise in contact stress. Removal of only 15–34% of the meniscus can produce a 350% increase in contact stress (Seedhon B, Hargreaves, D: Transmission of the load in the knee joint with special references to the role of the menisci: II. Experimental results, discussion, and conclusions. *Engineering in Med.*, 8:220 (1979)). Therefore, preservation of meniscal tissue and successful lesion repair are the goals of most current treatment methods for meniscal injury.

Currently, a meniscal transplantation is one of the available treatment options for patients whose injury, such as a meniscal tear, is severe and complex. Fresh-frozen allograft menisci have been shown to successfully attach and heal to the recipient periphery in experimental models. Studies have also shown evidence of repopulation of the allograft with host-derived cells. The clinical studies show that 71% of meniscal transplants result in complete healing at 8 months post operation. Despite these positive results, issues with availability of allograft tissue, tissue rejection, disease transmission and a lack of long-term data have limited the use of this approach.

The ability of a meniscal lesion to heal, either spontaneously or after surgical repair, is influenced by the proximity of the tear to the limited vascular supply, the size and complexity of the tear, and the presence of concurrent ligamentous instability. Lesions located in the peripheral 10–25% of the meniscus, in so called red zone where vascularity is greatest, have the greatest chance for successful repair. Lesions in the remaining avascular region of the meniscus, so called white zone, have shown only limited capacity, if at all, for repair and healing.

Recognizing the importance of the formation of a fibrin clot to the healing process, several researchers have used an autologous clot to enhance repair of avascular meniscal lesions. Using a canine model with stable 2 mm diameter defects filled with a fresh blood clot, fibrous reparative tissue was observed to fill in the defect site. The clot was thought to provide a scaffold for cell migration and proliferation, as well as chemotactic and mitogenic stimuli such as platelet-derived growth factor and fibronectin. However, in these studies, the histological appearance of the reparative tissue was notably significantly different from normal meniscus. Furthermore, cells migrating into the clot did not appear to synthesize a significant amount of extracellular matrix (*Amer. J. Sports Med.*, 17:393–400 (1989)). Consequently, the reported clinical results performed with autologous clots do not have a very positive outcome.

Moving toward a regenerative approach, more recent work has been directed at developing a resorbable porous collagen scaffold to replace the injured portion of the meniscus when repair is not possible. These scaffolds provide a substrate for migration and repopulation by native cells. See, for example, U.S. application Ser. Nos. 10/626,459, 10/104,677, 10/625,822, 10/625,245 and 10/882,581, by inventors, all hereby incorporated by reference.

Using a canine partial meniscectomy model and an appropriately shaped collagen implant, Stone and co-workers demonstrated that 63% of the implants showed evidence of substantial meniscal regeneration at 12 months (Stone K R, Rodkey W G, Weber R J, Meniscal regeneration with copolymeric collagen scaffolds: In vitro and in vivo studies evaluated clinically, histologically, and biochemically *Am. J. Sports Med.*, 20:104–111 (1992)). In these studies, histologically, the repair tissue seemed similar to normal canine meniscus. The limited clinical results for this approach indicated that regeneration of some meniscus-like tissue could be possible for patients with severe meniscal injuries who would have otherwise have to undergo partial or total meniscectomies.

The studies, described in the above cited patent applications, have shown that through the use of a fibrin clot or other appropriate scaffold material, replacement fibrocartilage can form through cellular integration, proliferation and tissue ingrowth. The regenerative treatment approach provides an appropriate follow-up to meniscectomy, potentially preventing cartilage degradation while restoring the function of the joint. Many meniscal tears in the avascular region are initially small and cause minor discomfort to the patient and, consequently, a significant number of the meniscal tears are left untreated due to the lack of fast, reliable arthroscopic repair techniques which would preserve the functional integrity of the meniscus. Over time the size of these tears grows and cause significant cartilage damage, as well as pain and loss of joint mobility.

To overcome the above stated problems, the current invention provides a minimally invasive method for repair of meniscal tear utilizing an arthroscopic procedure to introduce at the site of the meniscal injury a collagen-PEG hydrogel, preferably supplemented with a source of intra-articular fibroblastic cells or a support matrix which guides repair of the meniscal tear. Thus, the current invention provides a conservative alternative to partial meniscectomy.

All patents, patent applications and publication cited herein are hereby incorporated by reference.

SUMMARY OF THE INVENTION

One aspect of this invention concerns a method for minimally invasive repair of meniscal injuries and tears.

Another aspect of this invention concerns a method for repair of meniscal injuries using an arthroscopic procedure to introduce a collagen-PEG hydrogel alone or in admixture with a source of intra-articular fibroblastic cells or with a support matrix which guides repair of the meniscal tear.

Still another aspect of this invention concerns a method for use of collagen-PEG hydrogels with strong adhesive properties as a means for repair and regeneration of the meniscus and meniscal tissue.

Still yet another aspect of this invention concerns the method for restoration of the fibrillar network in the injured meniscal tissue wherein such restoration is enhanced by addition of collagen microfibrils prior to polymerizing of the collagen-PEG hydrogel wherein the rate of polymerization of the hydrogel can be further controlled by changing pH of the collagen-PEG hydrogel.

Another aspect of this invention concerns a method for repair of the meniscal tissue utilizing the collagen microfibrils in conjunction with the collagen-PEG hydrogel wherein said hydrogel promotes the cross-linking of the collagen microfibrils with the broken ends of fibrillar collagen network of the meniscus and wherein the collagen microfibrils in turn enhance the adhesive function of the collagen-PEG hydrogel by their chemical bonding to said hydrogel.

Still another aspect of this invention concerns a method for the restoration of true meniscal tissue and the ability of larger tears to heal wherein said restoration is enhanced by the addition of support matrix, with or without absorbed collagen hydrogel in its interior, wherein said support matrix is affixed to the lesion or tear with the adhesive hydrogel resulting, under these conditions, in Type I collagen and S-GAG accumulation and microfibril proliferation throughout the support matrix.

Still another aspect of this invention concerns a method for repair of the meniscal tissue by adding the patient's own pleuropotent cells to the collagen-PEG hydrogel that promotes differentiation of meniscal cells in situ wherein the surgeon, during the operation, can optionally remove and prepare suspension from synovial tissue or other source of fibroblasts and mix it with the hydrogel before administration of the hydrogel into the lesion or meniscal tear.

Another aspect of this invention concerns a method for repair of the meniscal tissue by utilizing a clot from the patient's own blood mixed with the hydrogel to provide autologous growth factors for the stimulation of extracellular matrix production.

Still yet another aspect of this invention concerns a method for repair of the meniscal lesions or tears by mixing the hydrogel with a suspension of the synovial tissue, fibroblasts and autologous growth factors obtained from the patient's blood cloth.

BRIEF DESCRIPTION OF THE DRAWINGS

FIG. 1 is a photograph showing a porcine meniscus in culture.

FIG. 2 is a photograph of the meniscus with tear sites indicated by A, B, and C.

FIG. 3A is a photograph of the tear region (4x) without treatment. FIG. 3B is a photograph of the tear region (10x) without treatment. Scale is 250 μm.

FIG. 4A is a photograph of the tear region (4x) showing a suture treatment. FIG. 4 is a photograph of the tear region (10x) showing a site of the suture.

FIG. 5A shows a microphotograph of a site of the meniscus treated with collagen-PEG hydrogel (4x). FIG. 5B is a microphotograph of a site of the meniscus treated with collagen-PEG hydrogel (10x) showing a cell integration.

FIG. 6 shows a Sinclair swine medial meniscus.

DEFINITIONS

As used herein:

"Collagen-PEG hydrogel" or "hydrogel" means any compound falling within the scope of this definition containing collagen and a hydrogel polymer such as polyethylene glycol (PEG) or derivatized polyethylene glycol, such as, for example, 4-armed polyethylene glycols derivatized with succinimidyl ester and thiol, plus methylated collagen (U.S. Pat. No. 6,312,725 B1, Nov. 6, 2001) or a protein, such as albumin, which is preferably cross-linked with a collagen compound. The hydrogel of the invention typically gels and/or bonds rapidly upon contact with tissue, particularly with tissue containing collagen.

"Support matrix" means biologically acceptable and biodegradable material suitable for introduction into a meniscal tear or lesion that provides a structural support for growth and three-dimensional propagation of cells. The support matrix is prepared from such materials as Type I collagen, Type II collagen, Type IV collagen, gelatin, agarose, cell-contracted collagen containing proteoglycans, glycosaminoglycans or glycoproteins, fibronectin, laminin, bioactive peptide growth factors, cytokines, elastin, fibrin, synthetic polymeric fibers made of poly-acids such as polylactic, polyglycolic or polyamino acids, polycaprolactones, polyamino acids, polypeptide gel, copolymers thereof and combinations thereof. The gel solution matrix may be a polymeric thermo-reversible gelling hydrogel. The support matrix is preferably biocompatible, biodegradable, hydrophilic, non-reactive, has a neutral charge and be able to have or has a defined structure.

DETAILED DESCRIPTION OF THE INVENTION

The current invention is based on findings that when a meniscal lesion, tear or another injury is treated with an adhesive composition comprising collagen-PEG hydrogel alone or in combination with other regeneration promoting components or accelerants, the meniscal tear may be advantageously healed without major invasive surgical procedure.

This invention, therefore, relates to a method for repair of meniscal lesions, tears and injuries. The invention utilizes approach of a minimally invasive procedure comprising induction of meniscal regeneration by introducing a strongly adhesive collagen-polyethylene glycol (PEG) hydrogel directly to a site of injury. The collagen-PEG hydrogels of the invention strongly bind the torn region of the meniscus for a period of time long enough needed for healing. They also promote cell migration and extracellular matrix formation in the torn zone.

More specifically, the invention concerns identification of adhesive hydrogel mixtures suitable for treatment of meniscal lesions, tears and injuries as well as identification of additional components aiding in such repair and in restoration of the meniscal functionality.

I. Meniscus

The meniscus is a dimorphic tissue. It consist of two distinctly different tissues, namely the red zone and the white zone.

The red zone, located at the meniscal periphery closest to a vascular blood supply, contains primarily cells that are morphologically fibroblastic. Additionally, the red zone contains much less of extracellular matrix than the white zone. Due to the proximity of the blood supply, lesions, tears and injuries in the red zone of the meniscus heal much more rapidly than those occurring in the white zone. Debridement and suturing of the lesions or tears can usually fully restore function to the red zone, including the restoration of the fibrillar network.

The injuries in the white zone of the meniscus, on the other hand, are currently almost completely untreatable. The white zone has no blood supply and is not in the proximity of the blood supply. It contains cells that look like chondrocytes typically observed in the articular cartilage, however, the ratio of extracellular matrix to cells is 10× that of articular cartilage. It is well known that the articular cartilage also does not have any blood supply and that the injuries in the articular cartilage are very difficult to treat and if they heal the ensuing cartilage is inferior fibrocartilage. In this regard the white zone of the meniscus resembles the articular cartilage.

II. Meniscal Injuries and Treatment Thereof

Meniscal injuries, particularly those in the white zone, seriously impair lifestyle of a patient. They can result in altered knee joint function, pain and permanent damage to the adjacent articular cartilage. A significant proportion of meniscal lesions or tears do not heal spontaneously or upon surgical repair due to the avascular nature of the inner white zone region of the meniscus, as described above. Left alone, these lesions and tears can propagate into larger defects that exacerbate cartilage damage and the knee function.

Currently and typically, to treat the injured meniscus, a partial or total meniscectomy is performed. The meniscus removal, however, reduces the stability of the joint and exposes the articular cartilage surfaces to higher contact stresses. Consequently, the aim of the research leading to this invention was to develop a unique, minimally invasive approach comprising induction of regeneration of the meniscal tissue by introducing to the site of the injury the highly adhesive collagen-PEG hydrogel. Such highly adhesive hydrogel fills the gap of the lesion or tear and holds it together preventing further damage to the meniscus and adjacent articular cartilage. It also provides means for a rapid repair meniscal tears and minimizes the degeneration of the articular surfaces of the knee.

A method according to the invention aids this regeneration process by inducing and supporting restoration of the fibrillar network in the red zone, however, the method of the invention is especially useful for the treatment of injuries in the avascular white zone, where meniscal lesions or tears normally do not heal and if they do heal, the fibrillar collagen network that provides the protective resistance to the tear or lesion that exemplifies the ruggedness and functionality of the meniscus is normally not restored. White zone lesions and tears thus require more than close approximation of the lesion surfaces by suturing in order to heal.

It has now been discovered that both the red but particularly the white zone lesions and tears may be repaired by introducing to a site of the meniscal injury a highly adhesive material comprising collagen and PEG polymer hydrogel complex. The regeneration process and healing of the tears in the red and white zone may be further augmented by addition of other components which will accelerate or aid this process.

III. Collagen Polyethylene Glycol Hydrogel Complex

A highly adhesive hydrogel complex according to the invention comprises a mixture of at least collagen or derivatized collagen and polyethylene glycol or derivatized polyethylene glycol. Other components, such as fibroblasts, synovial tissue, blood cloth or healing accelerators may be added to the complex. Additionally, structural hydrogel in form of the support matrix, for example collagen honeycomb, collagen sponge or collagen scaffold may be used in conjunction with the highly adhesive hydrogels.

The highly adhesive hydrogel such as, for example methylated collagen-PEG hydrogel, strongly binds the torn region during the period of healing and also permits or induces cell migration and extracellular matrix formation in the torn zone.

With respect to long-term binding, collagen-PEG hydrogel complex, particularly where the collagen is methylated collagen, has much stronger adhesive properties than PEG alone, collagen alone, or fibrin-based adhesives, and it is far more biocompatible than epoxies or gluteraldehyde cross-linked materials and the like. Additionally, since these collagen-PEG hydrogels are biologically acceptable and biodegradable, they biodegrade slowly and can thus remain at the site of injury for weeks or months without any detrimental consequences.

With respect to inducing cell migration and extracellular matrix formation, collagen-PEG hydrogels contain a network of Type I collagen which provides suitable environment for cell migration from surrounding native meniscal cells. Additionally, PEG is also a friendly substrate for cell migration.

Collagen-PEG hydrogels are complex mixtures containing collagen, collagen compounds or derivatized collagen, such as alkylated, for example methylated collagen, and a hydrogel polymer such as, for example, 4-armed polyethylene glycols derivatized with succinimidyl ester and thiol, such as those described in the U.S. Pat. No. 6,312,725 B1, issued Nov. 6, 2001, hereby incorporated by reference.

A. Adhesive Hydrogels

The adhesive hydrogel is a biologically acceptable rapidly gelling synthetic compound having adhesive and/or gluing properties, such as derivatized polyethylene glycol (PEG) which is cross-linked with a collagen compound, typically alkylated collagen. Examples of suitable hydrogels are tetra-hydrosuccinimidyl or tetra-thiol derivatized PEG, or a combination thereof, commercially available from Cohesion Technologies, Palo Alto, Calif. under the trade name CoSeal™, described in *J. Biomed. Mater. Res Appl. Biomater.*, 58:545–555 (2001), or two-part polymer compositions that rapidly form a matrix where at least one of the compounds is polymeric, such as, polyamino acid, polysaccharide, polyalkylene oxide or polyethylene glycol and two parts are linked through a covalent bond, as described in U.S. Pat. No. 6,312,725B1, herein incorporated by reference, and cross-linked PEG with methyl collagen, such as a cross-linked polyethylene glycol hydrogel with methyl-collagen. The synthetic compound may be also PEG or derivatized polyethylene glycol and may also contain, for example, a protein, such as, for example, albumin. The hydrogel of the invention typically gels and/or bonds rapidly and strongly upon contact with meniscal tissue.

The invention is intended to include the use of all collagen-PEG hydrogels having strong adhesive properties.

B. Additives and Accelerants

In addition, the ability of the invention to restore the fibrillar network can be enhanced by mixing of various additives and accelerants whether of the autologous or non-autologous, biological or synthetic origin. For example, autologous collagen microfibrils comprising type I collagen can be added to the hydrogel complex prior to polymerizing of the hydrogel complex. The collagen microfibrils can be created by a variety of methods known in the art, such as for example, electrospinning techniques. When microfibrils are added to the hydrogel complex, the complex promotes crosslinking of the collagen microfibrils with the broken ends of fibrillar collagen network of the meniscus, and results in restoration of the meniscus to its full functionality. The collagen microfibrils, on the other hand, enhance the adhesive function of the collagen-PEG hydrogel by chemical bonding to it.

Endogenously present compounds, such as all suitable accelerants, growth factors, PDFG and typical blood components can be added to the adhesive hydrogel to stimulate rapid healing.

Since the meniscus has relatively low cellularity and a highly organized structure, additional cells and/or an appropriate support matrix may be advantageously added to achieve true healing and effective remodeling of an injury site.

Either the collagen-PEG hydrogel alone or the augmented collagen-PEG hydrogel complex is easily applied arthroscopically soon after injury occurs. No meniscal tissue need to be removed, preserving the limited cell population within the tissue and protecting the articular cartilage surfaces. The strong chemical bonds created by the collagen-PEG hydrogel in both approaches allow faster patient rehabilitation and an earlier return to normal activity.

Moreover, the regeneration of the meniscal tissue can be also achieved by adding the patients own pleuropotent cells that are likely to differentiate into meniscal cells in situ to the adhesive collagen-PEG hydrogel complex. For example, during the arthroscopic surgery, the surgeon can remove synovial tissue or other source of fibroblasts, mince or homogenize it, and mix it with the hydrogel complex. Clot from the patient's own blood can also be used, for example, by mixing it with the adhesive hydrogel to provide autologous growth factors for the stimulation of extracellular matrix production.

Additionally, the rate of polymerization of the hydrogel complex can be controlled by controlling the pH of the buffer by addition of the weak physiologically acceptable acid or base.

C. Support Matrix

The ability to achieve the restoration of true meniscal tissue and the ability of larger gaps to heal can be enhanced by emplacement of a support matrix into the lesion or tear gap. The support matrix can be porous Type I collagen, such as, for example the collagen honeycomb collagen scaffold or collagen sponge with or without absorbed collagen-PEG hydrogel or any other hydrogel in its interior prior to the emplacement. The support matrix is affixed to the approximated lesion with the selected hydrogel complex. Under these conditions, accumulation of Type I collagen and S-GAG and fibril proliferation all occur throughout the construct.

Support matrix may be any biologically acceptable and biodegradable material that provides a structural support for healing of the meniscal injury. The support matrix is prepared from such materials as Type I collagen, Type II collagen, Type IV collagen, gelatin, agarose, cell-contracted collagen containing proteoglycans, glycosaminoglycans or glycoproteins, fibronectin, laminin, bioactive peptide growth factors, cytokines, elastin, fibrin, synthetic polymeric fibers made of poly-acids such as polylactic, polyglycolic or polyamino acids, polycaprolactones, polyamino acids, polypeptide gel, copolymers thereof and combinations thereof. The gel solution matrix may be a polymeric thermo-reversible gelling hydrogel. The support matrix is preferably biocompatible, biodegradable, hydrophilic, non-reactive, has a neutral charge and be able to have or has a defined structure.

IV. Method for Treatment and Repair of Meniscal Injuries

The method of the invention is directed to treatment and repair of the meniscal injuries.

In practice, the surgeon determines a size of the meniscal tear or lesion and the extent of injury. Depending on the size of the tear or lesion, the surgeon decides if the injury will be treated just with the collagen-PEG hydrogel complex or if the support matrix needs to be deposited in conjunction with the collagen-PEG hydrogel.

In both instances, the collagen-PEG hydrogel is deposited into the tear or lesion either alone or optionally supplemented with collagenous microfibrils, synovial tissue suspension, growth hormones, growth mediators, blood components or other accelerants. For smaller size injuries, typically, the collagen-PEG hydrogel alone is deposited into the tear or lesion. For larger or complicated tears or lesions, the support matrix is deposited together with the collagen-PEG hydrogel. The collagen-PEG hydrogel may be deposited after the deposition of the support matrix or it may be introduced into the support matrix before its implantation into the tear.

In both instances, the tear or lesions are filled with the collagen-PEG hydrogel in situ during the arthroscopic surgery. Typically, the liquid collagen-PEG hydrogel gels upon contact with tissue, fills the gap completely and attaches itself to the meniscal walls surrounding the tear or lesion. There it remains until the tear or lesion closes and heals, typically within several weeks or months. Since the tear or lesion gap is filled, there is no friction between the two sides of the tear or lesion, there is no further deterioration and enlargement of the tear, nor there is an accompanying deterioration of the adjacent articular cartilage.

For this kind of treatment, the surgeon performs a simple arthroscopy during which the liquid collagen-PEG hydrogel is deposited into the tear or lesion. Then the surgeon closes the incision and the patient is instructed to resume normal activity, such as walking or exercise within several days following the surgery. Walking is very important for healing of the meniscus as it applies the intermittent hydrostatic pressure to the healing meniscal tissue. Such hydrostatic pressure has been shown to support development of a new hyaline cartilage in articular joints, as disclosed by inventors in the U.S. application Ser. Nos. 10/626,459, 10/104,677, 10/625,822, 10/625,245 and 10/882,581, hereby incorporated by reference.

When the tears or lesions are larger, the second approach comprising deposition of the support matrix together with the collagen-PEG hydrogel is recommended. In this approach, depending on the clinical determination of the most effective treatment, the support matrix is either deposited first without having incorporated therein the collagen-PEG hydrogel, followed by deposition of the collegen-PEG hydrogel, or the support matrix incorporated with the collagen-PEG hydrogel prior to the surgery is deposited, as a complete structure, into the tear or lesion.

The current method for repair of the meniscal tears is only slightly invasive in that the arthroscopic deposition of the collagen-PEG hydrogel alone or complexed with the support matrix requires only a small incision for exact deposition of the hydrogel.

Following the surgery, the patient is encouraged to begin walking as soon as possible in order to apply the intermittent hydrostatic pressure onto deposited hydrogel. This leads to activation of the cells and their migration from the surrounding meniscal tissue into the hydrogel deposited within the tear. The attachment of the collagen-PEG hydrogel and cell migration were shown to be present, as described in the experimental studies section, upon deposition of the collagen-PEG hydrogel into the swine meniscus tear (C), wherein the attachment of the hydrogel to the walls of the meniscus tear and cell migration were both observed.

The current method is practical, very little invasive, safe and almost painless for the patient.

V. Experimental Studies

Experimental studies were performed to determine optimal conditions for meniscal tear treatability.

The first specific aim of the research was to determine the effectiveness of repairing tears in the avascular zone of the meniscus using collagen-PEG hydrogel with strong adhesive properties. Following activation by an accelerant, the collagen-PEG hydrogel will crosslink with the native collagen to create a strong chemical bond at the injury site. The collagen-PEG hydrogel material is, over time, remodeled and replaced with oriented fibrocartilaginous tissue.

In the first study, collagen-PEG hydrogel consisting of a polyethylene glycol (PEG)-collagen (Type I) co-polymer was be evaluated for meniscal repair. Unlike fibrin glue, collagen-PEG hydrogel co-polymers are capable of rapidly developing significant adhesive strength in situ. A crosslinking reaction between the collagen-PEG hydrogel and native collagen is initiated, providing a strong chemical bond at the interface. Currently, this type of collagen-PEG hydrogel is being utilized by inventors to fasten tissue engineered cartilage constructs in load bearing areas of the knee joint. Under these challenging loading conditions, the collagen-PEG hydrogel successfully fixes the construct in place, allowing cellular migration and tissue ingrown.

PEG based matrices have been described previously for applications such as tissue sealants, barriers to post surgical adhesion formation and vehicles for local delivery of biologically active molecules. These matrices tend to swell measurably and be highly elastic and low in tensile strength. They also degrade rapidly and resist cellular attachment.

However, the currently disclosed combination of a PEG hydrogel with type I collagen produces a unique gel with significant tensile strength and greater chemical stability than the PEG gels alone. The collagen provides additional crosslinking sites on a larger, more rigid support matrix, resulting in increased strength, decreased swelling and slower degradation in aqueous environments. In addition, the presence of collagen in the collagen-PEG hydrogel creates a highly biocompatible material which provides a suitable matrix for cell attachment, migration and proliferation.

A. Organ Culture Study

The efficacy of the collagen-PEG hydrogel for treating meniscal tears was evaluated by inventors in an organ culture study.

The left knee from a skeletally immature swine was obtained from a local abattoir and the medial meniscus was harvested aseptically. Porcine meniscus in the organ culture is seen in FIG. 1. Three tears (A), (B) and (C), each approximately 5 mm in length, were created in the white zone of the meniscus, as seen in FIG. 2.

Three different treatments were used to repair the three tears in the meniscus. The treatments were as described in Table 1.

TABLE 1

Design of Organ Culture Study

| Group | Treatment |
|---|---|
| (A) | No treatment (control) |
| (B) | Sutures |
| (C) | Collagen-PEG hydrogel |

The tear (A) was used as a control and left without any treatment. The tear (B) was treated with sutures across the tear. The sutures are visible in FIG. 2. The tear (C) was treated with collagen-PEG hydrogel according to the invention.

After treatment, the meniscus was cultured for 2 weeks in Dulbecco's modified Eagle medium (F-12) with 10% fetal bovine serum and 1% penicillin-streptomycin. At the end of the culture period, tissue was harvested for histological evaluation. Samples were fixed with 4% paraformaldehyde and embedded in paraffin. Sections (10 µm thick) were stained with Hematoxylin and Eosin and Saffranin O.

The histological results are summarized in Table 2.

TABLE 2

Results from Organ Culture Study

| Group | Treatment | Results |
|---|---|---|
| A | No treatment (control) | No attachment, no cell integration |
| B | Sutures | No attachment, no cell integration |
| C | Collagen-PEG hydrogel | Attachment, some cell integration |

As seen in Table 2, the tear (A) shows no attachment and no cell integration. The same is observed in the tear (B) where again there is no collagen-PEG hydrogel attachment or cell integration. In the tear (C) treated with the collagen-PEG hydrogel, however, there is attachment of the hydrogel to the tissue in place where the tear was with some integration of cells also seen.

Representative sections of tears (A), (B) and (C), stained with Saffranin O, are shown in FIGS. 3–5.

After two weeks in culture, the untreated control tear (A), seen in FIGS. 3A (4× magnification) and 3B (10× magnification) and the sutured tear (B), seen in FIGS. 4A (4× magnification) and 4B (10× magnification) were observed to have an open gap between the margins of the lesion, with no significant tissue formation and attachment. In contrast, the tear (C), seen in FIGS. 5A (4× magnification) and 5B (10× magnification) treated with the collagen-PEG hydrogel showed intimate contact at the interface and hydrogel filled the tear site evidencing attachment of the hydrogel to the tear.

Furthermore, some cell migration into the region of the tear occurred for the treatment group (B). This indicates that the collagen-PEG hydrogel is capable of bonding with meniscal tissue and supporting cell ingrowth into it.

B. Meniscal Healing

Castrated male Sinclair swine are utilized in the study to examine meniscal healing. Examination in the laboratory shows that the anterior region of the medial meniscus (FIG. 6) is most surgically accessible for this study. The avascular zone of the medial meniscus in this animal extends radially from the inner rim of the medial meniscus into about one third of the body of the meniscus.

Using an open surgical approach, a 5 mM full thickness longitudinal lesion is created in the anterior half of both the left and right medial menisci, approximately 2–3 mM from the inner rim. This lesion is intended to simulate the common longitudinal type tear that frequently occurs in sports-related injuries. The substantial size of the lesion results in instability of the opposing edges of the meniscal tissue, challenging the healing process further.

Lesion repair is performed immediately, according to the treatments listed in Table 3.

TABLE 3

Meniscal Healing Study Treatment Groups

| Treatment Code | Description |
| --- | --- |
| C1 | No treatment |
| C2 | Sutures |
| A | Collagen-PEG hydrogel and sutures |
| B | Collagen-PEG hydrogel with minced |
| C | Collagen-PEG hydrogel with oriented |

There are five sites randomly assigned to each treatment group, with a total of 13 animals required for the study. In the untreated control group C1, the lesion is irrigated with sterile saline, photodocumented and the joint capsule and skin layers are closed without further intervention. The sutured control group C2 is repaired with several non-resorbing sutures evenly distributed along the length. This is followed by routine lavage, photodocumentation and closure of the surgical wound.

The collagen-PEG hydrogel is used to repair the meniscal lesion in experimental group (A). The lesion is opened with forceps and approximately 0.5 cc of the collagen-PEG hydrogel is applied to the contacting faces. The accelerator is subsequently added to activate the crosslinking reaction. The forceps are removed and the lesion is allowed to close naturally. After allowing five minutes for the adhesive to bond, several nonresorbing sutures are applied along the length of the lesion. The site is lavaged, photodocumented and closed.

Lesion repair in the (B) group is augmented with minced synovial tissue, providing a source of intra-articular fibroblastic cells. Approximately 0.5 cc of fibrous connective tissue is harvested intra-operatively from the knee joint capsule and minced aseptically. The tissue and 0.5 cc of collagen-PEG hydrogel is then mixed thoroughly. The lesion is held open with a forceps and the collagen-PEG hydrogel mixture is dispensed into the site. Following addition of the crosslinking accelerator, the forceps are removed and the collagen-PEG hydrogel is allowed to bond for five minutes. The lesion is then sutured closed using several nonresorbing sutures. The site is lavaged, photodocumented and closed.

For the (C) group, an oriented collagen sponge support matrix is placed in the lesion in an effort to guide generation of radial collagen fibers to strengthen the lesion interface. The collagen support matrix has a parallel micro-tubular structure, with the long axis of the tubules facing perpendicular to the direction of the lesion. This type of collagen support matrix has been used successfully by inventors to guide articular cartilage formation under hydrostatic pressure. The support matrix material is cut intraoperatively to fit the size of the torn area. The width of the support matrix is 0.5 mM. The tubules are coated with the collagen-PEG hydrogel prior to insertion into the lesion. Additional collagen-PEG hydrogel is applied to the margins of the lesion once the support matrix is in place. Following addition of the crosslinking accelerator, lesion is released and the collagen-PEG hydrogel is allowed to bond for five minutes. The lesion is then sutured closed using several nonresorbing sutures. The site is lavaged, photodocumented and closed.

Following post-operative recovery, the animals are allowed to move about their enclosures freely without immobilization of the operated knee joint. Any observations of stiffness, lameness, or inactivity is recorded on a daily basis, along with general observations about the overall health of the animal. At two months post-op, the animals are anesthetized and the meniscal lesions are examined arthroscopically for evidence of healing. The lesion site is gently probed with a blunt instrument to assess tissue union at the margins of the lesion. The femoral surface of the medial meniscus and the articular cartilage on the opposing femoral condyle is also visually inspected for signs of fibrillation or other degenerative changes.

At four months post-op, all animals are euthanized and the knee joints are harvested. Following careful dissection, the medial meniscus are isolated and its gross appearance is documented. The appearance of the contact regions of articular cartilage surfaces on the medial femoral condyle and medial tibia plateau is also examined and documented.

The effects of the treatments on repair of the lesion site is assessed through histological evaluation. Axial cross section slices is obtained through the lesion site and stained with hematoxylin and eosin, as well as Saffranin O, to determine the cellularity and quality of the repair tissue within the lesion. The cellular phenotype in the lesion and the region surrounding is characterized. At least three sections from each lesion is blindly scored according to a grading scheme developed from the method reported by Whatley et al. (*J. Arthroscopic Rel. Sur.*, 16(2):127–136 (2000)) (Table 4).

TABLE 4

Quantitative Histological Grading Scheme

| Grade | Extracellular matrix organization within the lesion | Margin Contact |
| --- | --- | --- |
| 1 | Disorganized or discontinuous fibrous tissue | <50% fill |
| 2 | Disorganized but more continuous fibrocartilage | <70% fill |
| 3 | Organized continuous fibrocartilage | 100% fill |

The grading scale is indicative of the quality of the repair tissue, with 3 being the highest quality tissue which is expected to provide the strongest, most durable lesion interface. Statistical comparisons among treated and control specimens are made using analysis of variance.

What is claimed is:

1. A method for repair of meniscal injury, lesion or tear by introducing into a site of the meniscus injury, lesion or tear an adhesive rapidly gelling biodegradable derivatized collagen-PEG hydrogel complex wherein said derivatized collagen is alkylated Type I collagen.

2. The method of claim 1 wherein said collagen-PEG hydrogel complex further comprises Type I collagen microfibrils.

3. The method of claim 1 wherein the collagen-PEG hydrogel complex is further complemented with a growth factor.

4. The method of claim 1 wherein said collagen-PEG hydrogel complex is introduced into a site of the injury, lesion or tear alone or incorporated into a support matrix.

5. The method of claim 4 wherein the support matrix is a Type I collagen, Type II collagen, Type IV collagen, gelatin, agarose, cell-contracted collagen containing proteoglycan, glycosaminoglycan, glycoprotein, fibronectin, laminin, bioactive peptide growth factor, cytokine, elastin, fibrin, synthetic polymeric fiber made of poly-acid, polycaprolactone, polyamino acid, polypeptide gel or a copolymer thereof or a combination thereof.

6. The method of claim 4 wherein the support matrix is a Type I or Type II collagen honeycomb, sponge or scaffold.

7. The method of claim 4 wherein the support matrix is the Type I collagen honeycomb.

8. The method of claim 6 wherein the support matrix is the Type I collagen scaffold.

9. The method of claim 6 wherein the support matrix is the Type I collagen sponge.

10. The method of claim 1 wherein the alkylated collagen is methylated collagen.

11. The method of claim 1 wherein the polyethylene glycol is derivatized or non-derivatized.

12. The method of claim 11 wherein the polyethylene glycol is non-derivatized.

13. The method of claim 11 wherein the polyethylene glycol is derivatized with succinimidyl ester, tetra-thiol, tetra-hydroxysuccinimidyl or albumin.

14. The method of claim 10 wherein the collagen-PEG hydrogel complex introduced into the site of the meniscus injury, lesion or tear further comprises autologous cells.

15. The method of claim 1 wherein said derivatized collagen-PEG hydrogel complex is introduced into the site of the meniscus injury, lesion or tear and the injury, lesion or tear is further treated with sutures.

16. The method of claim 1 wherein the said derivatized collagen-PEG hydrogel complex introduced into the site of the meniscus injury, lesion or tear further comprises a synovial tissue.

17. The method of claim 1 wherein said derivatized collagen-PEG hydrogel complex is incorporated into a support matrix and said matrix is introduced into the site of the meniscus injury, lesion or tear and said injury, lesion or tear is further treated with sutures.

* * * * *